United States Patent
Mintz et al.

(10) Patent No.: US 11,872,328 B2
(45) Date of Patent: Jan. 16, 2024

(54) DEVICES, KITS AND METHODS FOR REDUCING AND/OR PREVENTING INTRA-ABDOMINAL ADHESIONS

(71) Applicants: HADASIT MEDICAL RESEARCH SERVICES AND DEVELOPMENT LTD., Jerusaelm (IL); AZRIELI COLLEGE OF ENGINEERING JERUSALEM, Jerusalem (IL)

(72) Inventors: Yoav Mintz, Jerusalem (IL); Nikolai Kunicher, Pardesia (IL); Tali Tavor Re'em, Modiin (IL)

(73) Assignees: HADASIT MEDICAL RESEARCH SERVICES AND DEVELOPMENT LTD., Jerusalem (IL); AZRIELI COLLEGE OF ENGINEERING JERUSALEM, Jerusalem (IL)

( * ) Notice: Subject to any disclaimer, the term of this patent is extended or adjusted under 35 U.S.C. 154(b) by 0 days.

(21) Appl. No.: 16/643,061

(22) PCT Filed: Aug. 28, 2018

(86) PCT No.: PCT/IL2018/050949
§ 371 (c)(1),
(2) Date: Feb. 28, 2020

(87) PCT Pub. No.: WO2019/043699
PCT Pub. Date: Mar. 7, 2019

(65) Prior Publication Data
US 2020/0330210 A1    Oct. 22, 2020

Related U.S. Application Data

(60) Provisional application No. 62/551,831, filed on Aug. 30, 2017.

(51) Int. Cl.
*A61F 2/00*    (2006.01)
*A61L 31/04*    (2006.01)
(Continued)

(52) U.S. Cl.
CPC .......... *A61L 31/042* (2013.01); *A61F 2/0063* (2013.01); *A61K 31/734* (2013.01); *A61K 33/14* (2013.01); *A61F 2002/0072* (2013.01)

(58) Field of Classification Search
None
See application file for complete search history.

(56) References Cited

U.S. PATENT DOCUMENTS

| | | |
|---|---|---|
| 5,788,641 A | 8/1998 | Policastro et al. |
| 6,150,581 A | 11/2000 | Jiang et al. |

(Continued)

FOREIGN PATENT DOCUMENTS

| | | |
|---|---|---|
| CA | 2860193 | 3/2015 |
| EP | 2740500 | 6/2014 |

(Continued)

OTHER PUBLICATIONS

Fang et al. Multiple steps and critical behaviors of the binding of calcium to alginate. J. Phys. Chem B 2007, 111, 2456-2462 (Year: 2007).*

(Continued)

*Primary Examiner* — Lakshmi S Channavajjala
(74) *Attorney, Agent, or Firm* — The Roy Gross Law Firm, LLC; Roy Gross

(57) ABSTRACT

Disclosed herein are devices/kits and methods for reducing, treating, preventing or eliminating post-operative adhesions in an intervention/target site within a body of a subject. The method comprises the steps of: introducing an applicator, configured for applying an anti-adhesive composition, into an intervention/target site within a body of a subject; apply- (Continued)

ing the anti-adhesive composition onto the intervention/target site; and extracting the applicator from the body of the subject, wherein the method is performed during or following an interventional procedure.

12 Claims, 12 Drawing Sheets

(51) Int. Cl.
*A61K 31/734* (2006.01)
*A61K 33/14* (2006.01)

(56) References Cited

U.S. PATENT DOCUMENTS

| | | |
|---|---|---|
| 6,673,093 B1 | 1/2004 | Sawhney |
| 6,827,689 B2 | 12/2004 | Lin |
| 8,417,306 B2 | 4/2013 | Cheng |
| 8,998,818 B2 | 4/2015 | Pranevicius et al. |
| 9,398,943 B2 | 7/2016 | Criscuolo et al. |
| 9,731,046 B2 | 8/2017 | Cohen et al. |
| 2001/0032099 A1 | 10/2001 | Joao |
| 2006/0159823 A1 | 7/2006 | Melvik et al. |
| 2011/0054296 A1 | 3/2011 | McCarthy et al. |
| 2011/0097367 A1* | 4/2011 | Wallrapp ............... A61P 13/00 514/8.5 |
| 2011/0119078 A1 | 5/2011 | Cotter et al. |
| 2011/0293692 A1* | 12/2011 | Bennett ................ A61L 31/145 424/447 |
| 2013/0109947 A1 | 5/2013 | Wood |
| 2015/0335675 A1 | 11/2015 | Cohen et al. |
| 2016/0166504 A1* | 6/2016 | Jarrett .................... A61K 9/50 424/490 |

FOREIGN PATENT DOCUMENTS

| | | | |
|---|---|---|---|
| JP | H11253547 A * | 9/1999 | ............ A61C 19/06 |
| WO | 2014124520 | 8/2014 | |
| WO | 2015167807 | 5/2015 | |

OTHER PUBLICATIONS

Matoba, et al., "Prevention of Polyglycolic Acid-Induced Peritoneal Adhesions Using Alginate in a Rat Model", BioMed Research International, (2015).

Majumder, et al., "Evaluation of a novel permanent capped helical coiled fastener in a porcine model of laparoscopic ventral hernia repair", Surgical Endoscopy, vol. 30, pp. 5266-5274 (2016).

Gruber-Blum, et al., "Liquid anti-adhesive agents for intraperitoneal hernia repair procedures: Artiss® compared to CoSeal® and Adept® in an IPOM rat model", Surgical Endoscopy, vol. 31, pp. 4973-4980 (2017).

International Search Report and Written Opinion of the Searching Authority, International Application No. PCT/IL2018/050949, dated Nov. 28, 2018.

\* cited by examiner

DEVICES, KITS AND METHODS FOR REDUCING AND/OR PREVENTING INTRA-ABDOMINAL ADHESIONS

CROSS REFERENCE TO RELATED APPLICATIONS

This application is a National Phase of PCT Patent Application No. PCT/IL2018/050949 having International filing date of Aug. 28, 2018, which claims the benefit of priority of U.S. Provisional Application No. 62/551,831 filed on Aug. 30, 2017. The contents of the above applications are all incorporated by reference as if fully set forth herein in their entirety.

TECHNICAL FIELD

The present disclosure relates generally to the field of surgery, particularly to that of utilizing surgical meshes.

BACKGROUND

Surgical meshes may be used during both laparoscopic and open surgery for repair of many types of defects and injuries. While the overlay meshes in open surgery are fixed in place by sutures, the inlay meshes in laparoscopy are fixed using tacks which are placed on the mesh to hold it in place to the abdominal wall. The meshes may be used to provide support to surrounding tissue.

Surgical meshes are commonly used in the repair of an abdominal wall hernia which is a defect in all layers of the abdominal wall through which intraperitoneal content, most frequently parts of omentum or bowel, may protrude. During hernia repair laparoscopic surgery, a mesh may be placed intra-abdominally, therefore serving as a barrier preventing abdominal organs from protruding through the abdominal wall and may further serve as a reinforcement of the abdominal wall strength.

Adhesions are fibrous bands of scar tissue that form between internal organs and tissues, joining them together abnormally. A common form of adhesion occurs after surgery as a result of trauma, although adhesion may occur as a result of other processes or events such as pelvic inflammatory disease, mechanical injury, radiation treatment and the presence of a foreign material. Postoperative adhesions frequently occur following abdominal surgery and are a leading cause of intestinal obstruction.

As foreign bodies, such as meshes, are a specific lead point for adhesion formation, hence the prevention of adhesions is of concern when foreign bodies are placed intraperitoneally. This has been achieved both experimentally and clinically by interposition degradable compounds such as polyglactin, hyaluronate and cellulose, among others. Most commonly, the design includes the addition of a sheet-like barrier shielding the mesh structure from the abdominal organs. These barriers are available both in absorbable and permanent forms. Apart from these composite meshes, other designs have focused on constructing more chemically inert materials such as titanium coated plastics or new polymers, as well as biologic materials such as bovine or cadaver dermal matrixes. These meshes are extremely expensive due to their coating materials and processing. Nevertheless, even with these highly expensive meshes designed specifically for intraperitoneal use, adhesions are still encountered in differing degrees of extent and intensity.

Alginate is an anionic polysaccharide derived from brown algae (seaweed). Alginate is composed of uronic acids (guluronic (G) and mannuronic (M) acids) that undergoes gelation (without the need of heating) in the presence of bivalent cations, such as $Ca^{2+}$, $Ba^{2+}$, $Mg^{+2}$ or any other bivalent cation or combination of cations. Acid gels may also develop at low pH.

Gelling occurs when the divalent cations take part in the interchain ionic binding between guluronic acids blocks (G-blocks) in the polymer chain giving rise to a three-dimensional network. Such binding zones between the G-blocks are often referred to as egg-boxes, and consequently alginates with a high content of G-blocks induce stronger gels. Gels made of M-rich alginate are softer and more fragile, and may also have a lower porosity. This is due to the lower binding strength between the polymer chains and to the higher flexibilities of the molecules.

Alginate is a biomaterial that has found numerous applications in biomedical science and engineering due to its favorable properties, including biocompatibility and ease of gelation. Alginate hydrogels have been particularly attractive in wound healing, drug delivery, and tissue engineering applications to date, as these gels retain structural similarity to the extracellular matrices in tissues.

SUMMARY

Aspects of the disclosure, in some embodiments thereof, relate to devices and methods for reducing, preventing or eliminating post-operative/post-surgical tissue adhesions in a target site (which may also be referred to as an intervention site) by in-situ application of an anti-adhesion composition (e.g., alginate) onto the intervention/target site and implants therewithin. The devices and methods may be utilized to substantially reduce, prevent, or eliminate tissue to tissue adhesions and/or adhesions between tissue and medical implants (e.g., surgical meshes) in the surgical intervention/target site. According to some embodiments, the in-situ application of the anti-adhesion cover/coating onto the medical implant is performed post-placement of the implant in the target site. Advantageously, the method of the present invention is performed in a simple and cost-effective manner.

Medical implants and surgical instruments may be pre-coated by anti-adhesive coats to prevent adhesion of a tissue to the implants. A potential problem of pre-coated medical implants may be damage of the coating during the delivery and placement of the medical implant (e.g., mesh). Advantageously, the post placement coating of the medical implant utilized by the disclosed devices and methods facilitates convenient delivery, manipulation, and positioning of a pre-coated (for example, non-coated) medical implant. Further, post placement coating facilitates coating only the surface of the mesh that faces the organs, while refraining from coating the surface in contact with the tissue, to which it is attached.

Another potential problem of the pre-coated medical implants may be adhesion of the tissue to the implant's surrounding such as adhesion of a tissue to another tissue within the surrounding or adhesion of the tissue to attachment elements of the medical implants (e.g., tacks). In a non-limiting example, when a surrounding tissue of the intervention site, which is not intended to be covered by the medical implant (e.g., surgical mesh), is injured during the interventional procedure (e.g., by a surgical instrument), this tissue may form adhesions. Advantageously, post placement coating utilizing the disclosed devices and methods may be applied onto the medical implant and its surrounding such as an attachment element and/or the surgery target site to prevent adhesion formation.

The medical implant may include, in accordance with some embodiments, a surgical mesh, surgical clips, vessel grafts, gastric restrictive devices, such as the Laparoscopic Adjustable Gastric Band, stapler lines following organ resection like bowel or lung or any other medical implant. Surgical mesh may include, for example, plastic mesh such as Prolene, Mersilene or other types of plastic mesh, Gortex mesh, Collagen mesh, Composites material mesh or any other type of surgical mesh.

There is provided, according to some embodiments, a method for reducing, treating, preventing or eliminating post-operative adhesions in a target site within a body of a subject (e.g., a body lumen), the method comprises the steps of: introducing an applicator, configured for applying an anti-adhesive composition, into a target site within a body of a subject; applying the anti-adhesive composition onto the target site; and retracting the apparatus from the body of the subject, wherein the method is performed during or following an interventional procedure.

There is provided, according to some embodiments, a device comprising a reservoir configured for storing/containing an anti-adhesive composition; and an applicator configured for introducing/dispensing the anti-adhesive composition within a body of a subject, wherein the device is configured for insertion into the body of a subject.

There is provided herein, according to some embodiments, a method for reducing, treating, preventing or eliminating post-operative adhesions in a target site within a body of a subject, the method comprising: introducing an applicator, configured for applying an anti-adhesive composition, to a target site within a body of a subject; applying the anti-adhesive composition onto an implanted medical device positioned in the target site, wherein the method is performed during or following an interventional medical procedure.

The method may further include deploying and fixing the implant in the target site prior to applying the anti-adhesive composition thereon. The method may further include applying the anti-adhesive composition to a tissue and/or an organ in the vicinity of the implanted medical device. The method may further include retracting the applicator from the body.

There is provided herein, according to some embodiments, a medical device for reducing, treating, preventing or eliminating post-operative adhesions in a target site within a body of a subject, the device comprising: a reservoir configured for storing an anti-adhesive composition; and an applicator fluidly connected to the reservoir and configured for introducing the anti-adhesive composition to a target site within a body of a subject.

There is provided herein, according to some embodiments, a medical device for coating an intra-abdominal mesh comprising: a reservoir configured for storing an anti-adhesive composition; and an applicator fluidly connected to the reservoir and configured for introducing the anti-adhesive composition to the intra-abdominal mesh positioned at a target site within a body of a subject. The device may further include a temperature regulator for regulating the temperature of the anti-adhesive composition within the reservoir and/or within the applicator.

In some embodiments, the medical implant may include a surgical mesh. In some embodiments, the medical implant may further include one or more mesh fixation element. In some embodiments, the medical implant may include a tissue fixation element.

The method may further include deploying and fixing the mesh in the target site prior to applying the anti-adhesive composition thereon.

In some embodiments, the target site may be within an abdominal cavity.

According to some embodiments, the anti-adhesive composition may include alginate.

According to some embodiments, the interventional procedure is selected from a group consisting of: a minimally invasive surgical procedure and an open surgery. The minimally invasive surgical procedure may be selected from a group consisting of: a laparoscopic surgical procedure, an arthroscopic surgery and an endoscopic surgical procedure. The interventional procedure may be a laparoscopic hernia (repair) surgery.

There is provided herein, according to some embodiments, a kit comprising: a reservoir containing an anti-adhesive composition; and an applicator configured to be fluidly connected to the reservoir and configured for introducing the anti-adhesive composition to a target site within a body of a subject. The kit may further include a medical implant. The medical implant may include a surgical mesh. The kit may further include a mesh fixation element. The mesh fixation element may include a tack, a surgical suture or both. The anti-adhesive composition may include alginate. The anti-adhesive composition may further include a solvent, a carrier, an excipient or any combination thereof. The anti-adhesive composition may further include an active pharmaceutical ingredient selected from the group consisting of antibiotics, antiseptic and anti-inflammatory substances.

There is provided herein, according to some embodiments, a method for reducing, treating, preventing or eliminating post-operative adhesions in a target site within a body of a subject, the method includes: introducing an applicator, configured for applying an anti-adhesive composition, to a target site within a body of a subject; applying the anti-adhesive composition onto an implanted medical device positioned in the target site, wherein said method is performed during or following an interventional medical procedure. According to some embodiments, applying may also be referred to as in-situ applying.

According to some embodiments, the method may further include applying the anti-adhesive composition to a tissue and/or an organ in the vicinity of the implanted medical device.

According to some embodiments, the medical implant may include a surgical mesh. The medical implant may further include a mesh fixation element.

According to some embodiments, the method may further include deploying and fixing the mesh in the target site prior to applying the anti-adhesive composition thereon.

According to some embodiments, the method may further include retracting the applicator from the body.

According to some embodiments, the target site is within an abdominal cavity.

According to some embodiments, the anti-adhesive composition includes alginate.

Alginate is a linear copolymer with homopolymeric blocks of (1→4)-linked b-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks) or alternating M and G-residues (MG-blocks).

In some embodiments, the term "alginate" may include alginic acid or any ester, salt (such as, but not limited to, sodium salt), modification or derivative thereof. In some embodiments, the terms "alginate", "alginic acid" and "algin" may be used interchangeably.

The alginate may include alginate having a MW in the range of <75 kDa (lower than 75 kDa), (such as FMC Biopolymers (Drammen, Norway) PRONOVA UP VLVG alginate, which may also be referred to herein "VLVG alginate"), alginate having a MW in the range of about 75-200 kDa (such as FMC Biopolymers (Drammen, Norway) PRONOVA UP LVG alginate, which may also be referred to herein "LVG alginate"), alginate having a MW>200 kDa (such as FMC Biopolymers (Drammen, Norway) PRONOVA UP MVG alginate, which may also be referred to herein "MVG alginate"), alginate having a MW>200 kDa and G/M ratio ≤1 (such as FMC Biopolymers (Drammen, Norway) PRONOVA UP MVM alginate), alginate having a MW in the range of 75-200 kDa and G/M ratio ≤1 (such as FMC Biopolymers (Drammen, Norway) PRONOVA UP LVM alginate) or any other type of alginate or any combination thereof.

According to some embodiments, the anti-adhesive composition may further include a crosslinker. The crosslinker may include bivalent cations. The bivalent cations may include $Ca^{2+}$, $Ba^{2+}$, $Mg^{+2}$ or a combination thereof. The $Ca^{2+}$ cations may originate from calcium gluconate, calcium chloride ($CaCl_2$)) or a combination thereof.

According to some embodiments, the anti-adhesive composition may include non-crosslinked or partially crosslinked alginate having a low MW, for example, <75 kDa, such as PRONOVA UP VLVG alginate of FMC Biopolymers (Drammen, Norway), alginate having a high MW, for example, about 100 kDa, for example, at a range of 50-400 kDa such as PRONOVA UP LVG alginate of FMC Biopolymers (Drammen, Norway) or any combination thereof.

According to some embodiments, the alginate may have a MW of about 5-20 10-30, kDa, 10-100 kDa, 50-200 kDa, 100-300 kDa, 50-350 kDa, 100-200 kDa, or 50-400 kDa.

According to some embodiments, the non-crosslinked or partially crosslinked alginate used (for example, LVG alginate) may have a concentration of about 0.5-2.5% (w/v), for example, 0.7-2.0% (w/v), 1.0-1.5% (w/v), or 0.8-1.2% (w/v). According to some embodiments, the concentration of the $Ca^{2+}$ (in the non-crosslinked or partially crosslinked alginate) cations may be about 0.25-1% (w/v), for example, 0.3-0.7% (w/v), 0.32% (w/v). According to some embodiments, the concentration of the $Ca^{+2}$ cations may be higher (e.g., 5-30% (w/v)), particularly if $CaCl_2$) is used in situ.

According to some embodiments, the non-crosslinked or partially crosslinked alginate used (for example, VLVG alginate) may have a concentration of about 1.0-5.0% (w/v) for example 2.0-3.0% (w/v). According to some embodiments, the concentration of the $Ca^{+2}$ cations may be about 0.5-3.0% (w/v), for example, 0.6%-1.1% (w/v).

According to some embodiments, (in situ) applying the anti-adhesive composition onto the implanted medical device comprises the following steps: a. applying a first composition comprising an anti-adhesive substance; and b. applying, onto the first composition, a second composition comprising a crosslinker; thereby, in-situ, increasing the viscosity of the first composition. According to some embodiments, the anti-adhesive substance includes non-crosslinked or partially crosslinked alginate According to some embodiments, the crosslinker includes a bivalent cation. According to some embodiments, the first composition comprises partially crosslinked alginate. For example, partially crosslinked LVG alginate at a $Ca^{+2}$ concentration of at least about 0.32% w/v or partially crosslinked VLVG alginate at a $Ca^{+2}$ concentration of at least about 0.75% w/v.

There is provided herein, according to some embodiments, a medical device for coating an intra-abdominal mesh for reducing, treating, preventing or eliminating post-operative adhesions in a target site within a body of a subject, the device includes: a reservoir configured for storing an anti-adhesive composition; and an applicator fluidly connected to said reservoir and configured for introducing the anti-adhesive composition to the intra-abdominal mesh positioned at a target site within a body of a subject. According to some embodiments, the device may further include a temperature regulator for regulating the temperature of the anti-adhesive composition within the reservoir and/or within the applicator and/or further comprising an additional reservoir comprising a crosslinker.

There is provided herein, according to some embodiments, a kit for in-situ coating an intra-abdominal mesh for reducing, treating, preventing or eliminating post-operative adhesions in a target site within a body of a subject, the kit includes: a first reservoir containing an anti-adhesive composition comprising hydrogel; and an applicator configured to be fluidly connected to said reservoir and configured for introducing the anti-adhesive composition to a target site within a body of a subject. According to some embodiments, the kit may further include a surgical mesh. According to some embodiments, the kit may further include one or more mesh fixation elements. According to some embodiments, the hydrogel comprises non-crosslinked or partially crosslinked alginate.

The alginate may include alginate having a MW in the range of 5-50 kDa, alginate having a MW in the range of 50-400 kDa or any other type of alginate or any combination thereof.

According to some embodiments, the hydrogel composition (e.g., partially crosslinked alginate) may include a crosslinker. The crosslinker may include bivalent cations. For example, the bivalent cations may include $Ca^{2+}$, $Ba^{2+}$, $Mg^{+2}$ or a combination thereof. The $Ca^{2+}$ cations may originate from calcium gluconate, calcium chloride ($CaCl_2$)) or a combination thereof.

According to some embodiments, the non-crosslinked or partially crosslinked alginate used may have a concentration of about 0.5-2.5% (w/v), for example, 0.7-2.0% (w/v), 1.0-1.5% (w/v), or 0.8-1.2% (w/v). According to some embodiments, the concentration of the $Ca^{2+}$ cations (in the non-crosslinked or partially crosslinked alginate) may be about 0.25-1% (w/v), for example, 0.3-0.7% (w/v), 0.32% (w/v). According to some embodiments, the concentration of the $Ca^{2+}$ cations may be higher (e.g., 10-30% (w/v)), particularly if $CaCl_2$) is used in situ.

According to some embodiments, the non-crosslinked or partially crosslinked alginate used may have a concentration of about 1.0-5.0% (w/v) for example 2.0-3.0% (w/v). According to some embodiments, the concentration of the $Ca^{2+}$ cations may be about 0.5-3.0% (w/v), for example, 0.6%-1.1% (w/v).

According to some embodiments, the kit further includes a second reservoir comprising a crosslinker. The crosslinker may include about 1M $CaCl_2$) or about 0.5-10% w/v (e.g., 1-5%, 2-3% or 3%) Ca Gluconate (D-Gluconic acid).

In some embodiments, the target site is within a body lumen. In some embodiments, the target site may be intra-abdominal or intra-thoracic, or intra-luminal (for example, inside the gastrointestinal tract).

In some embodiments, the interventional procedure is selected from a group consisting of: a minimally invasive surgical procedure and an open surgery. In some embodiments, the minimally invasive surgical procedure is selected from a group consisting of: a laparoscopic surgical procedure, an arthroscopic procedure and an endoscopic surgical procedure. In some embodiments, the interventional procedure is a laparoscopic hernia (repair) surgery.

According to some embodiments, the anti-adhesive composition, e.g., alginate can be applied to the surface of the organ such as bowel, liver, spleen, lung, heart or any other organ, following minimally invasive or open surgery even without placing any mesh. This is to provide adhesion prevention due to the surgery itself that causes breakings in the smooth lining of the peritoneum or pleura.

In some embodiments, the applicator may be introduced to the target site within the body through natural lumens (e.g., gastroenterological, urinary or vaginal), percutaneous approaches, through the working channel of laparoscopes, or through the working channel of endoscopes.

In some embodiments, the anti-adhesive composition may include Dextran, Icodextrin, Hyaluronic acid, hyaluronic acid derivatives, cross-linked (modified) hyaluronan gel, hyaluronan, sodium Hyaluronate, carboxymethylcellulose, Polyethylene Glycol (PEG) based liquid precursors, chitosan, any derivative thereof or any combination thereof.

According to some embodiments, anti-adhesive composition, such as, but not limited to, alginate, may be utilized in a form of paste, lotion, hydrogel, emulsion, aerosols, droplets, powder or any other applicable form.

According to some embodiments, the term "hydrogel" as used herein refers to a network of natural or synthetic hydrophilic polymer chains capable of containing water. Non-limiting Examples of compounds capable to form such networks include alginate, modified alginate, a partially cross-linked alginate solution, chitosan, hyaluronan cross-linked, hyaluronic-based hydrogel, cross-linked modified hyaluronan or any modifications thereof.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Some embodiments of the disclosure are described herein with reference to the accompanying figures. The description, together with the figures, makes apparent to a person having ordinary skill in the art how some embodiments of the disclosure may be practiced. The figures are for the purpose of illustrative discussion and no attempt is made to show structural details of an embodiment in more detail than is necessary for a fundamental understanding of the teachings of the disclosure. For the sake of clarity, some objects depicted in the figures are not to scale.

DETAILED DESCRIPTION

Figure 1:
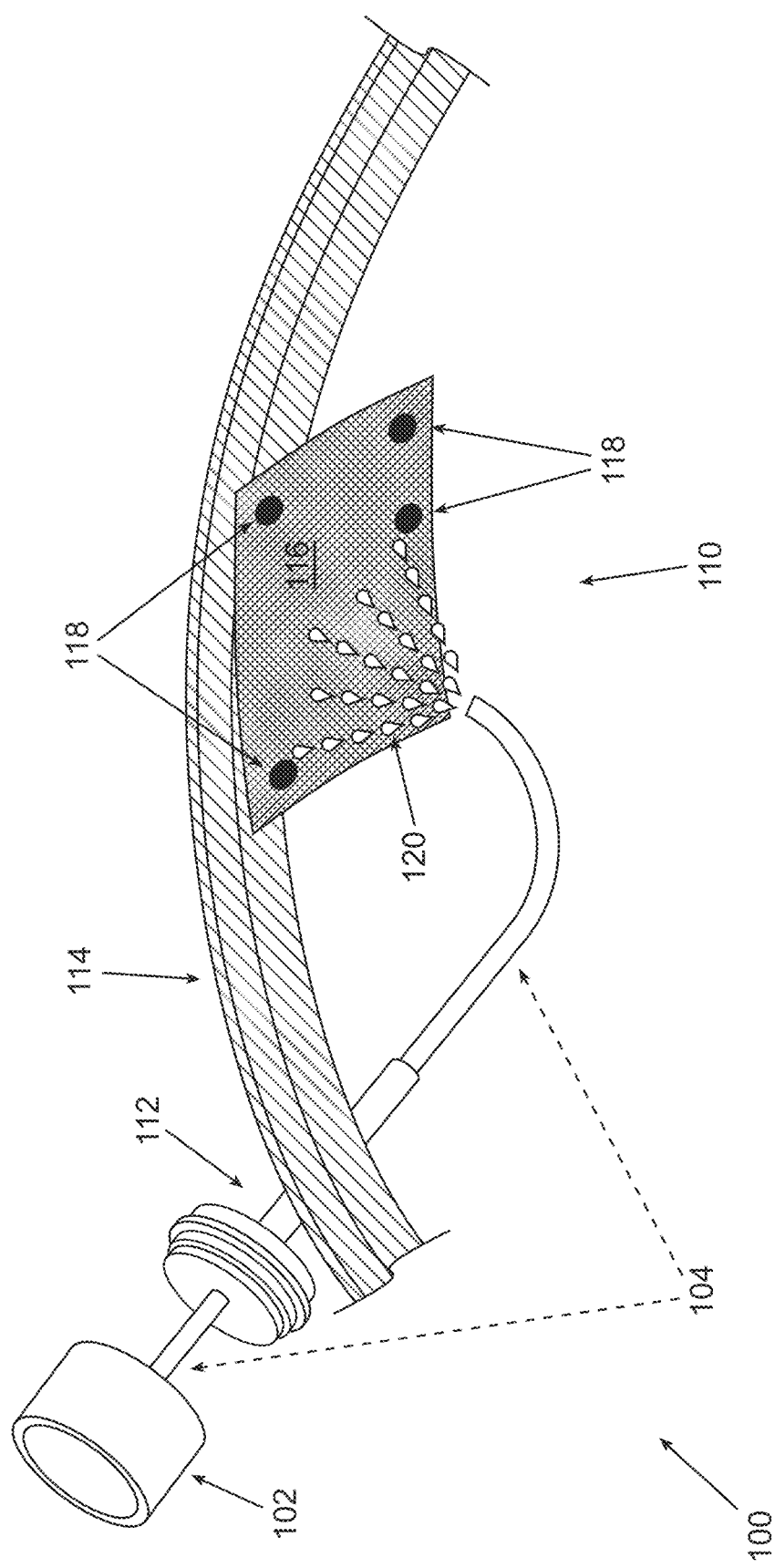
FIG. 1 schematically illustrates intra-abdominal application of an anti-adhesive composition onto a surgical mesh and tacks thereof in an intervention site, by a device/kit that may be used for reducing, treating, preventing or eliminating post-operative tissue adhesions, in accordance with some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

The principles, uses, and implementations of the teachings herein may be better understood with reference to the accompanying description and figures. Upon perusal of the description and figures present herein, one skilled in the art will be able to implement the teachings herein without undue effort or experimentation. In the figures, same reference numerals refer to same parts throughout.

In the description and claims of the application, the words "include" and "have", and forms thereof, are not limited to members in a list with which the words may be associated.

As used herein, the term "about" may be used to specify a value of a quantity or parameter (e.g. the length of an element) to within a continuous range of values in the neighborhood of (and including) a given (stated) value. According to some embodiments, "about" may specify the value of a parameter to be between 80% and 120% of the given value. For example, the statement "the length of the element is equal to about 1 m" is equivalent to the statement "the length of the element is between 0.8 m and 1.2 m". According to some embodiments, "about" may specify the value of a parameter to be between 90% and 110% of the given value. According to some embodiments, "about" may specify the value of a parameter to be between 95% and 105% of the given value.

As used herein, according to some embodiments, the terms "substantially" and "about" may be interchangeable.

The present disclosure relates generally to the field of post-operative adhesions, specifically to reduction, treatment, prevention or elimination of post-operative adhesions.

There is provided, according to some embodiments, a method for reducing, treating, preventing or eliminating post-operative adhesions in a target site within a body of a subject, the method comprising the steps of: introducing an applicator, configured for applying an anti-adhesive composition, into a target site within a body of a subject; applying the anti-adhesive composition onto the intervention/target site; and extracting the applicator from the body of the subject. In some embodiments, the application of the anti-adhesive composition is performed onto a medical implant within the target site and/or tacks thereof.

As referred to herein, the terms "patient" and "subject" may interchangeably be used and may relate to a subject that is or was subjected to an interventional medical procedure.

In some embodiments, the method is performed during or following an interventional procedure. In some embodiments, the interventional procedure is selected from a group consisting of: an open surgery, a laparoscopic surgery, an endoscopic surgery, an arthroscopic surgery and any combination thereof. In some embodiments, the interventional procedure includes placing a medical implant in the target site. In some embodiments, the medical implant is intraluminal implanted. The implant may be placed at the target site by endoscopic or laparoscopic delivery.

In some embodiments, the target site is within a body lumen. Non-limiting examples of body lumens include the gastrointestinal tract, e.g., esophagus, stomach, small intestine, or the colon. In some embodiments, the target site may be intra-abdominal.

In some embodiments, the applicator may be introduced to the target site within the body through natural lumens (e.g., gastroenterological, urinary or vaginal), percutaneous approaches, through the working channel of laparoscopes, or through the working channel of endoscopes.

In some embodiments, the anti-adhesive composition is applied directly onto the target site and/or the medical implant within the target site. In some embodiments, the anti-adhesive composition may be applied to the target site and/or the medical implant by pouring, spraying, sprinkling, mounting, coating and/or spreading of the anti-adhesive composition. Each possibility represents a separate embodiment. In some embodiments, the target site and/or the medical implant are immersed within the anti-adhesive composition.

In some embodiments, the anti-adhesive composition comprises alginate. In some embodiments, the anti-adhesive composition comprises alginate and a solvent, a carrier and/or an excipient. In some embodiments, the anti-adhesive composition comprises alginate and an active pharmaceutical ingredient, such as, but not limited to, antibiotics, antiseptic, anti-inflammatory or any other substance or combination of substances. In some embodiments, the anti-adhesive composition consists of alginate and a solvent (e.g., aqueous solvent).

The term "solvent" as used herein relates to any liquid which aids in dissolving or diluting any other substance, or a mixture of substances. One exemplary solvent is water. In some embodiments, the term "solvent" may encompass also a mixture of solvents.

There is provided, according to some embodiments, a device configured for insertion into a body of a subject and comprising: a reservoir configured for storing/containing an anti-adhesive composition; and an applicator configured for introducing the anti-adhesive composition within the body of the subject.

There is provided, according to some embodiments, a kit comprising: a reservoir configured for containing an anti-adhesive composition; and an applicator configured for introducing the anti-adhesive composition within the body of the subject.

Optionally, the applicator of the disclosed device/kit is configured to be fluidly connected to the reservoir. Optionally, the applicator includes a sprayer, a racket, a sprinkler, a nebulizer, or any combination thereof.

Optionally, the reservoir of the disclosed device/kit may include separate compartments each for a different component of the anti-adhesive composition. In a non-limiting example, alginate powder and a suitable solvent may be contained in different compartments and mixed together to form alginate gel to be applied onto the target site and/or the medical implant within the target site.

Throughout the following description, similar elements of different embodiments of the device/kit are referenced by element numbers differing by integer multiples of 100. For example, a reservoir of FIG. 1 is referenced by the number 102, and a reservoir of FIG. 2, which corresponds to reservoir 102 of FIG. 1, is referenced by the number 202.

Reference is now made to FIG. 1 which schematically illustrates intra-abdominal application of an anti-adhesive composition by a device/kit 100 that may be used for reducing, treating, preventing or eliminating post-operative tissue adhesions in an intervention/target site, in accordance with some embodiments.

Device/kit 100 includes a reservoir 102 configured to store an anti-adhesion composition, and an applicator 104 fluidly connected to reservoir 102 and configured for introducing the anti-adhesive composition within a body of a subject (e.g., within the abdominal cavity).

Applicator 104 is deployed within the abdominal cavity 110 via a laparoscopic trocar 112 inserted through the abdominal wall 114. Optionally, applicator 104 is deployed within the abdominal cavity 110 following intra-abdominal fixation of a mesh 116 to the abdominal wall 114 by utilizing tacks 118. Optionally, applicator 104 is positioned such as to allow application of the anti-adhesive composition onto mesh 116 and tacks 118. The applied flow of the anti-adhesive composition is indicated by dashed lines 120.

Figure 2:
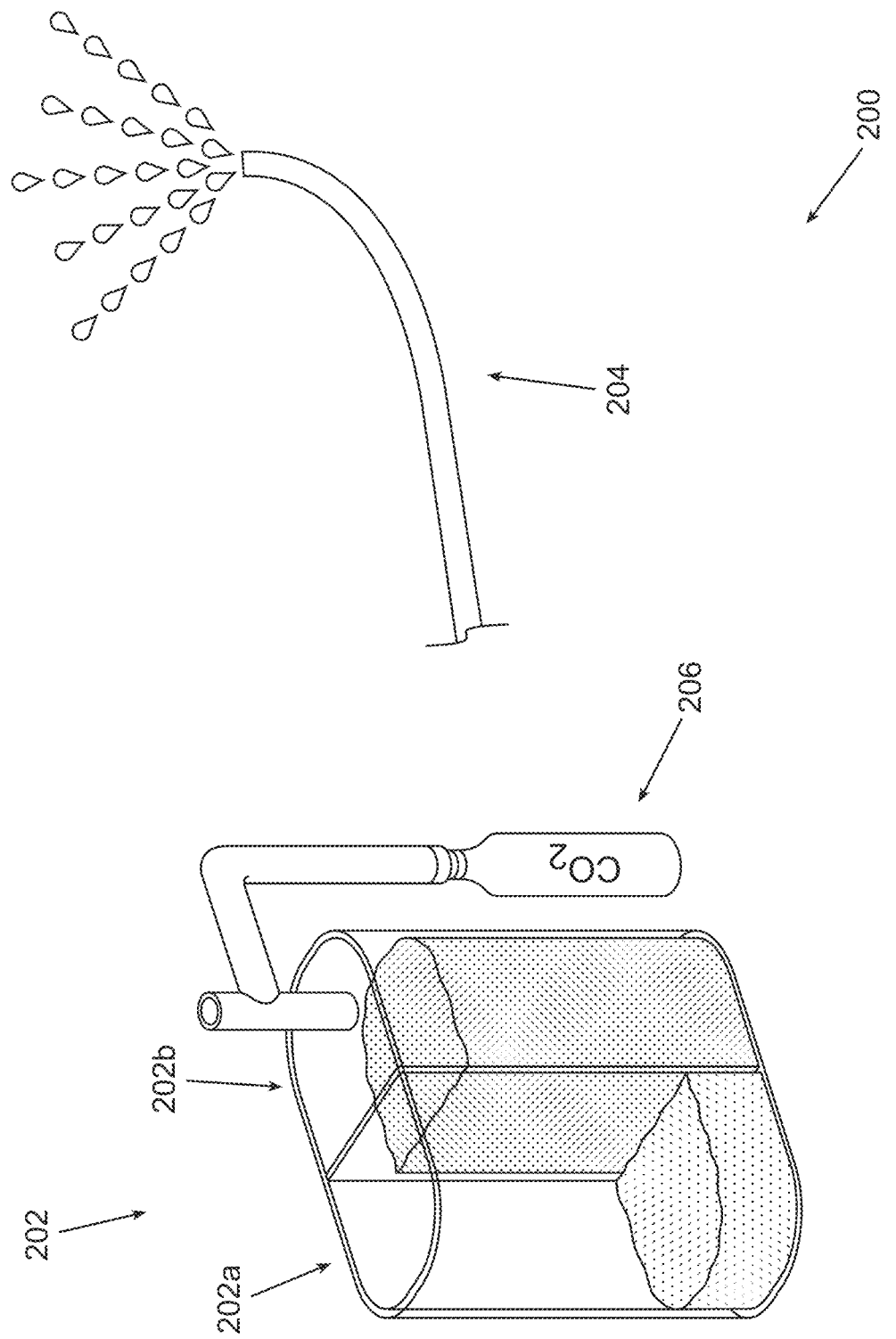
FIG. 2 schematically illustrates a device/kit for applying an anti-adhesive composition onto a target site, a surgical mesh and/or tacks thereof in an intervention site within a body of a subject, according to some embodiments.

Reference is now made to FIG. 2 which schematically illustrates a device/kit 200 that may be used for reducing, treating preventing or eliminating post-operative tissue adhesions in an intervention site within a body of a subject, in accordance with some embodiments.

Device/kit 200 includes a reservoir 202 (similar to reservoir 102 of FIG. 1) configured to contain an anti-adhesion composition and an applicator 204 configured to fluidly connect to reservoir 202 and configured for introducing the anti-adhesive composition within a body of a subject. Optionally, applicator 204 is designed as a spraying rod for spraying the anti-adhesive composition onto a desired surface. Notably, device 200 further includes a gas balloon 206 configured to pressure the anti-adhesive composition to enter applicator 204. It is noted that, in accordance with alternative embodiments, the reservoir (such as reservoir 102, 202, 302) may be connected to a $CO_2$ flow located in the operating room (OR) for the deployment of the alginate (or any other anti-adhesive composition) without the need of a gas balloon. Further, reservoir 202 includes two separate compartments 202a and 202b. Optionally, components of the anti-adhesive composition are separately stored in compartments 202a and 202b, and form the anti-adhesive composition upon mixing. In a non-limiting example, alginate gel is formed upon mixing of alginate powder stored in compartment 202a and a suitable solvent, such as water, which is stored in compartment 202b.

Figure 3:
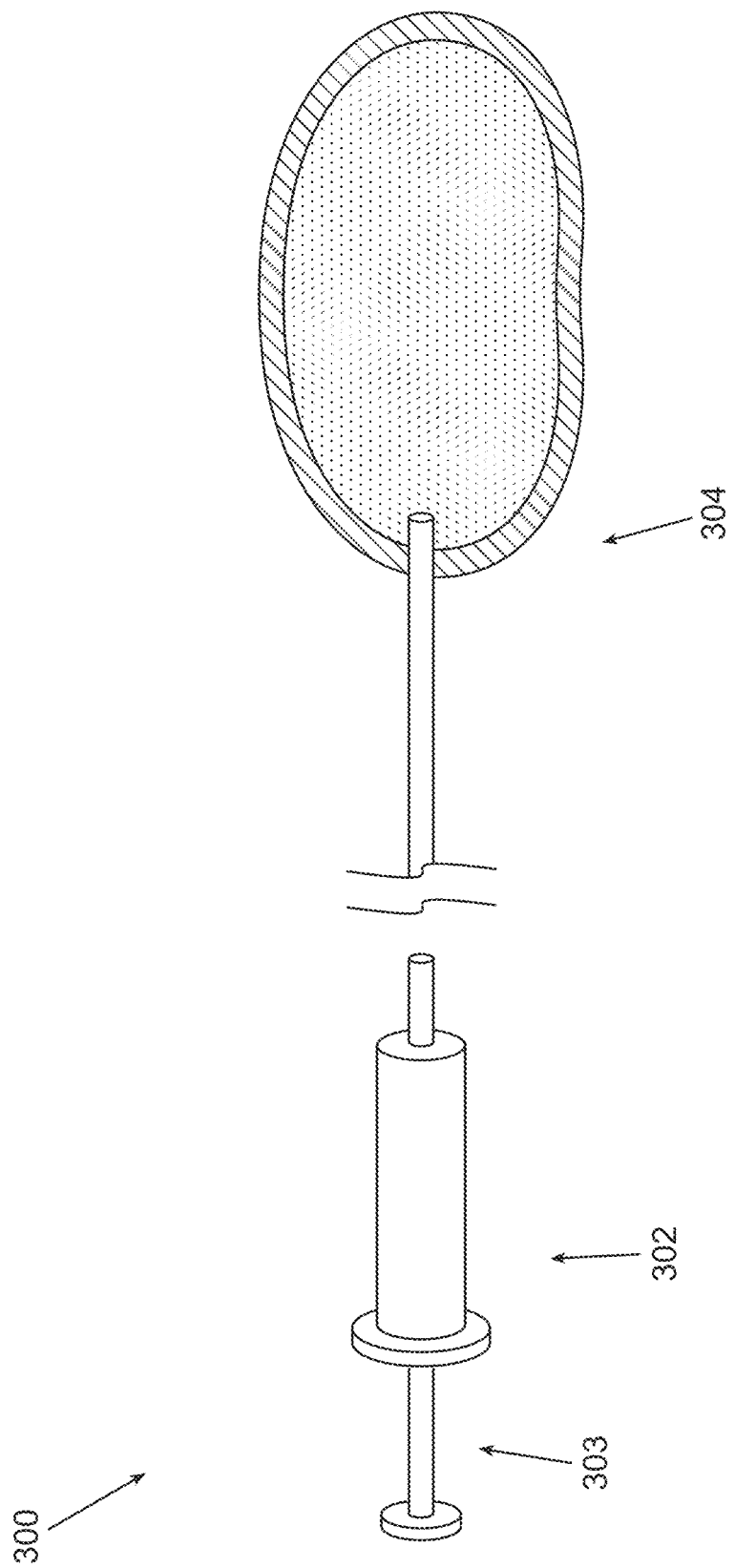
FIG. 3 schematically illustrates a device/kit for applying an anti-adhesive composition onto a target site, a surgical mesh and/or tacks thereof in an intervention site within a body of a subject, according to some embodiments.

Reference is now made to FIG. 3 which schematically illustrates a device/kit 300 that may be used for reducing, treating preventing or eliminating post-operative tissue adhesions in an intervention site within a body of a subject, in accordance with some embodiments.

Similarly to device/kit 100 of FIG. 1, device/kit 300 includes a reservoir 302 configured to contain an anti-adhesion composition and an applicator 304 configured to fluidly connect to reservoir 302 and configured for introducing the anti-adhesive composition within a body of a subject. Notably, applicator 304 is designed to be pressed against a desired surface in order to facilitate contact of the anti-adhesive composition, contained therewithin, with the desired surface. Reservoir 302 may include an internal plunger 303 for pushing the anti-adhesive composition into applicator 304.

Figure 4:
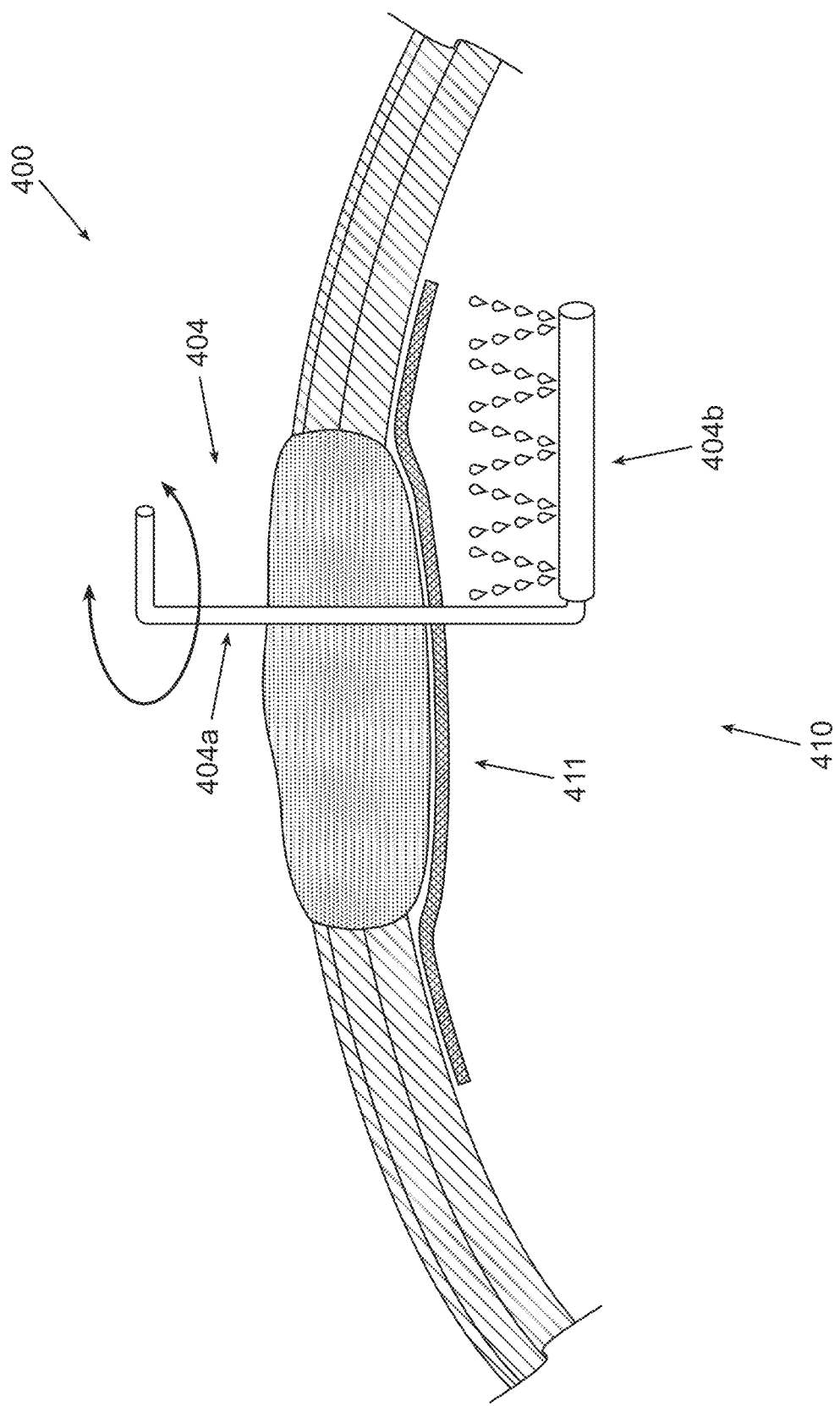
FIG. 4 schematically illustrates intra-abdominal deployment of a device/kit for applying an anti-adhesive cover onto a surgical mesh and/or tacks thereof in an intervention site within a body of a subject, according to some embodiments.

Reference is now made to FIG. 4 which schematically illustrates a device/kit 400 that may be used for reducing, treating, preventing or eliminating post-operative tissue adhesions in an intervention site, deployed within an abdominal cavity 410, in accordance with some embodiments.

Similarly to device/kit 100 of FIG. 1, device/kit 400 includes a reservoir (not shown) configured to store an anti-adhesion composition and an applicator 404 configured to fluidly connect to the reservoir and configured for introducing the anti-adhesive composition within a body of a subject. Notably, applicator 404 is designed as a sprinkler and includes a rod 404a and a sprayer 404b in fluid communication. As demonstrated in FIG. 4, rod 404a may be inserted into abdominal cavity 410 through the center of a desired surface area 411 to be covered by the anti-adhesive composition and circle the sprayer such that the anti-adhesive composition introduced via the sprayer is sprinkled onto desired surface area 411.

Figure 5:
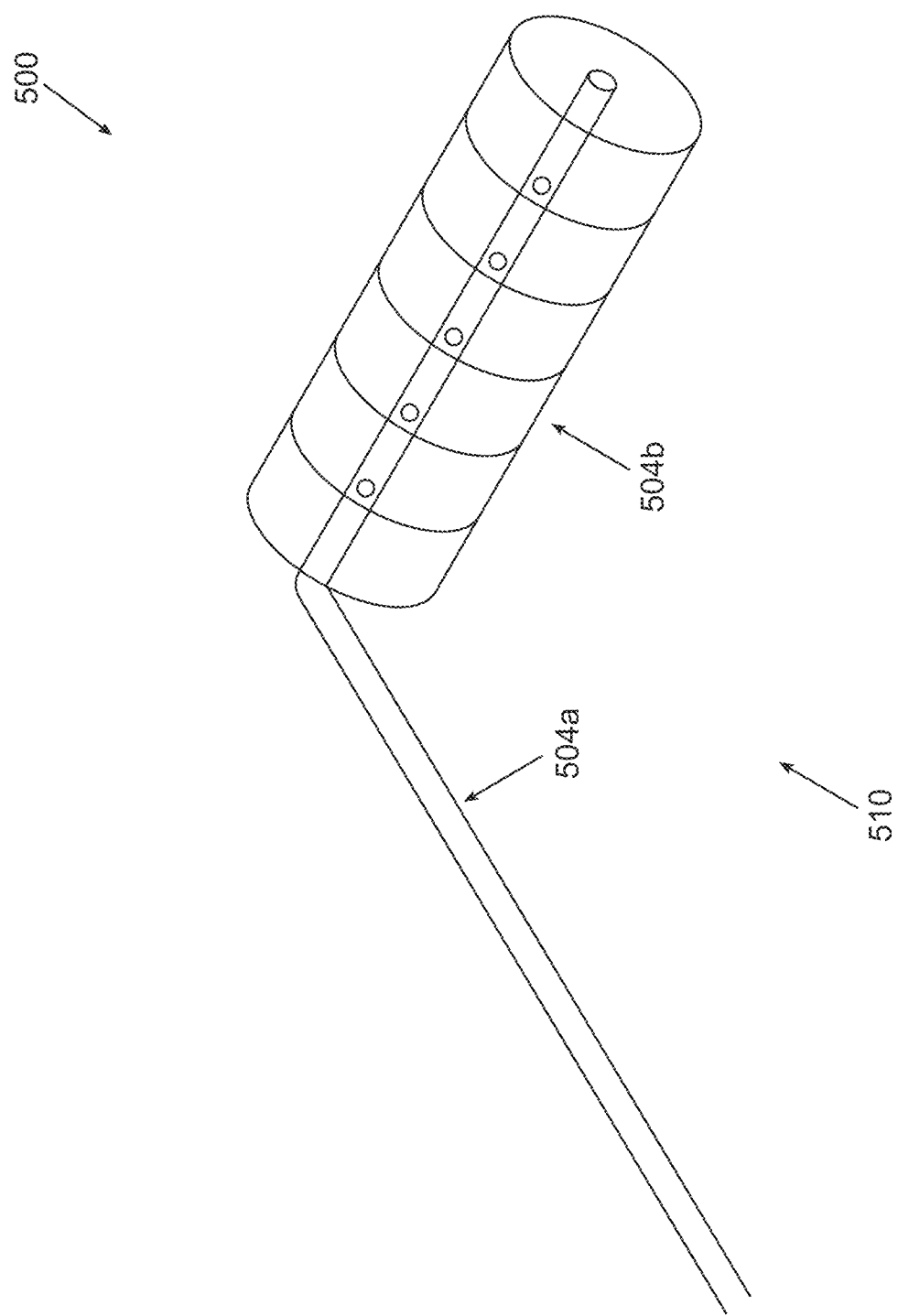
FIG. 5 schematically illustrates a device/kit for applying an anti-adhesive composition onto a target site, a surgical mesh and/or tacks thereof in an intervention site within a body of a subject, according to some embodiments.

Reference is now made to FIG. 5 which schematically illustrates a device/kit 500 that may be used for reducing, treating preventing or eliminating post-operative tissue adhesions in an intervention site within a body of a subject.

Similarly to device/kit 100 of FIG. 1, device/kit 500 includes a reservoir (not shown) configured to store an anti-adhesion composition and an applicator 510 configured to fluidly connect to the reservoir and configured for introducing the anti-adhesive composition within a body of a subject. Notably, applicator 510 includes a rod 504a and a rolling device ('roller') 504b fluidly connected to rod 504a and configured to be rolled over a desired surface and to introduce (via holes) the anti-adhesive composition, to facilitate spreading of the composition over the desired surface.

Figure 6:
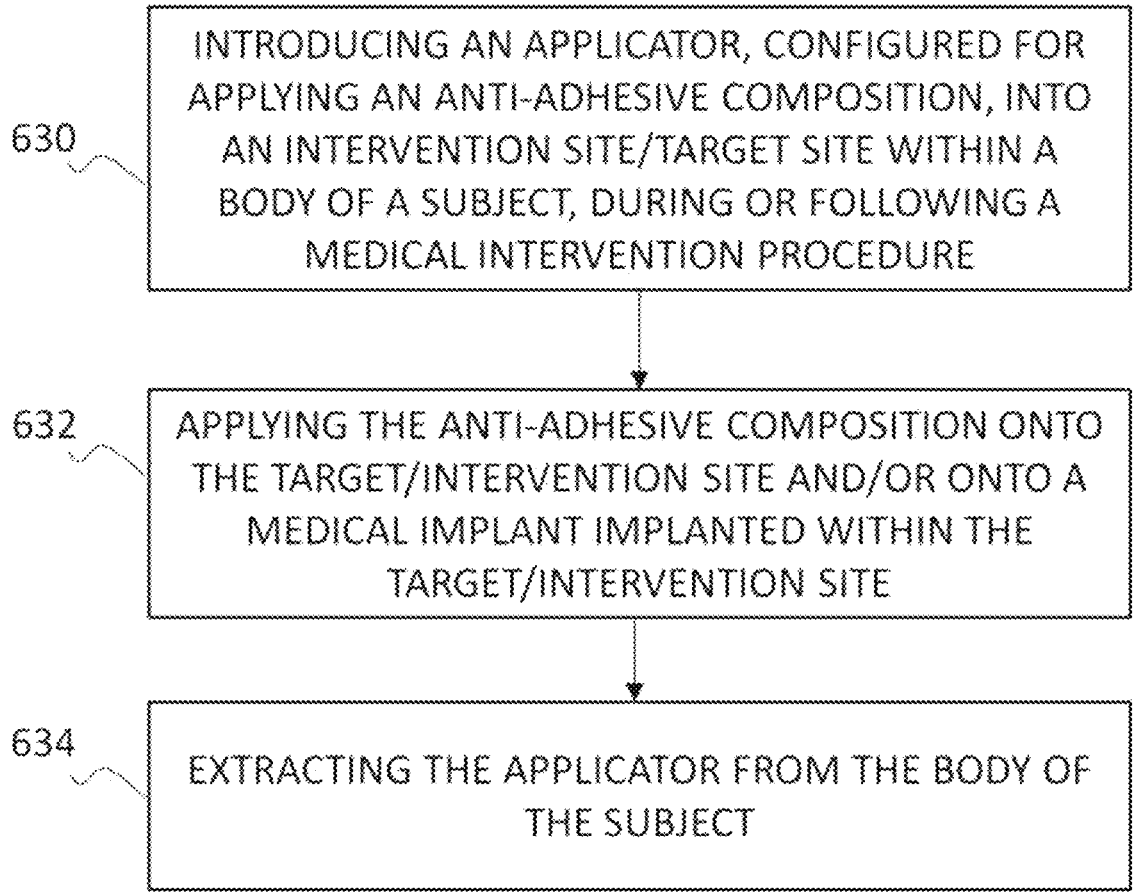
FIG. 6 is an illustrative flowchart of the method for applying an anti-adhesive cover onto a target site, a surgical mesh and/or tacks thereof in an intervention site within a body of a subject for reducing, treating, preventing or eliminating post-operative tissue adhesions, according to some embodiments.

Reference is now made to FIG. 6 which is a flowchart of a method for reducing, treating, preventing or eliminating post-operative tissue adhesions in an intervention site, in accordance with some embodiments. An applicator, configured for applying an anti-adhesive composition, is introduced into an intervention site/target site within a body of a subject, during or following a medical intervention procedure (step 630). The anti-adhesive composition is applied onto the target/intervention site and/or onto a medical implant implanted within the target/intervention site (step 632). The applicator is extracted from the body of the subject (step 634).

EXPERIMENTAL EXAMPLE

Example 1

The methods and systems described herein above, were experimentally tested. Specifically, the ability of alginate to reduce formation of tissue adhesions in the abdominal cavity following intra-abdominal mesh implantation was evaluated.

Rats were surgically implanted with meshes. Each rat underwent a surgical procedure in which two meshes were sutured to the internal side of its abdominal wall. Rats of the test group were further treated to cover the sutured meshes with an alginate gel. To this end, the alginate gel was prepared with commercially available alginate (Sigma) powder suspended in water. Following the procedure, the abdomen was sutured and rats of the control and test groups were recovered. 14 days after the surgery the abdominal cavities of rats of the control (untreated with alginate gel) and test groups (treated with alginate gel) were evaluated for formation of tissue adhesions to the implanted meshes.

Figure 7:
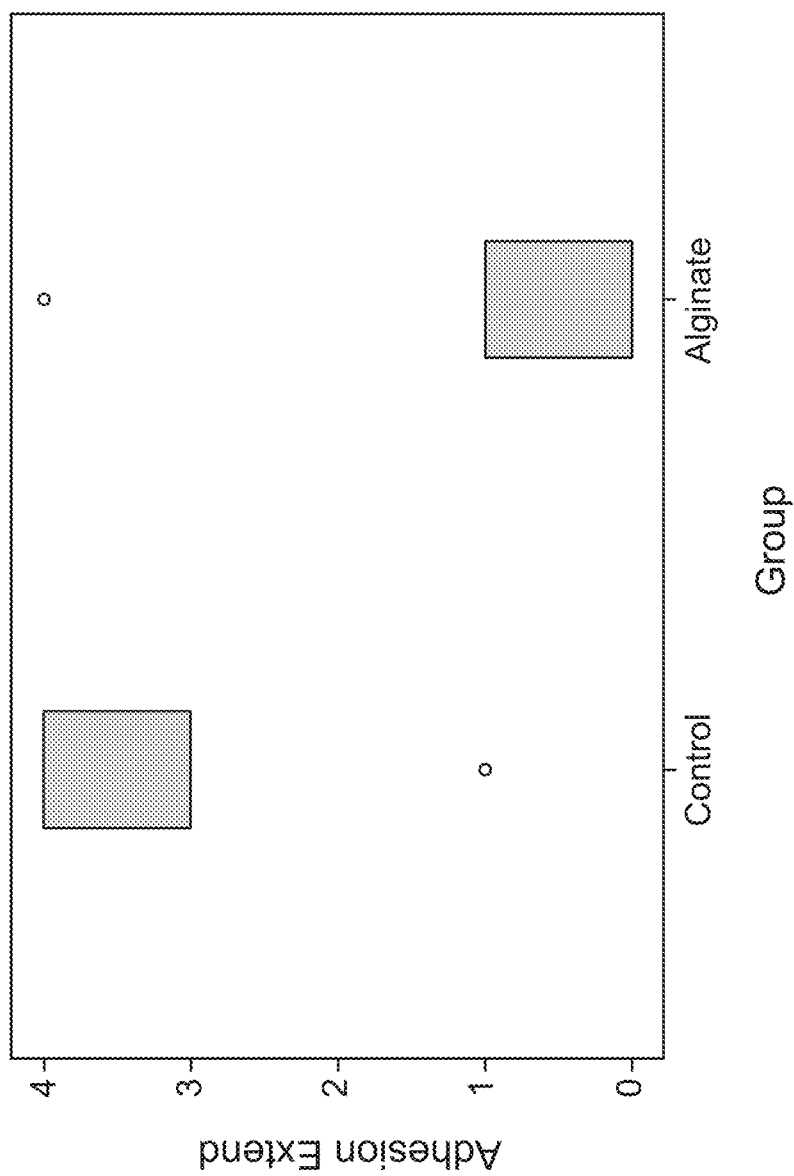
FIG. 7 is a box-plot scheme that shows experimental results of adhesion extent in rats implanted with meshes and untreated ('control') or treated ('alginate') with an alginate gel.

As demonstrated in FIG. 7, coverage of the meshes with organ adhesions such as intestine and liver was dramatically reduced from 75% to 6% by covering the meshes with alginate gel. These results confirmed that alginate gel can be utilized as a biomaterial preventing adhesions to the implanted mesh. As alginate production may be low cost, this substance can be used for mesh coating and dramatically reduce the cost of surgical interventions such as laparoscopic hernia surgery.

Example 2

Sodium alginates of high G content (VLVG, LVG, >60% guluronic acid monomer content) from FMC Biopolymers (Drammen, Norway) were utilized:

Molecular weights (MW):

VLVG alginate refers to low MW of about 30 kDa (range of 5-50 kDa) and LVG refers to high MW of about 100 kDa (range of 50-400 kDa).

Specific viscosities:

VLVG—5 mP*s (range of 1-20 mP*s or ≤20 mPa*s) and LVG—66 mPa*s (range of 20-200 mPa*s).

VLVG alginate formulations were prepared with various VLVG concentrations and various degrees of cross-linking. LVG alginate formulations were also prepared at low cross-linking concentration (0.2%) and at high cross-linking concentration (0.32%) to achieve gel. Analysis of the formulations is presented in Table 1 below.

The dynamic viscoelastic characterization of cross-linked alginate solution was carried out on a stress-control rheometer (TAINSTRUMENTS, model AR 2000), operated in the cone-plate mode with a cone angle of about 4° and a 40 mm diameter. Storage (G') and loss modulus (G") measurements were conducted in a frequency sweep range of 0.1-10 Hz, while viscosity was assessed at a shear rate range of (0.01-1000) $s^{-1}$.

The measuring device was equipped with a temperature unit (Peltier plate) to provide effective temperature control (±0.05° C.). Dynamic viscoelastic characterization was carried out at 25° C. and induction of gelation was determined by measuring the frequency dependence of storage (G') and loss modulus (G"). The viscosity (Pa*s) of the different formulations was also compared at a shear rate of 10 $s^{-1}$.

(such as composition "B−" presented in Table 1) may be administered on the mesh and, after the administration of this less viscous formulation, an additional amount of $Ca^{+2}$ Gluconate may be administered to formulate "B+" of 1.25% VLVG and 0.75% $Ca^{+2}$ (Table 1) to obtain a firm gel coating on the mesh. $Ca^{+2}$ concentrations indicated are concentrations after crosslinking. $Ca^{+2}$ may be administered, for example, in the form of calcium gluconate or in the form of $CaCl_2$) (e.g., 1M). Use of $CaCl_2$) may increase $Ca^{+2}$ concentrations with respect to $Ca^{+2}$ concentrations obtained by calcium gluconate.

Another example: partially-cross linked VLVG 1.2% (w/v) and 0.6% $Ca^{+2}$ (such as composition "A" presented in

TABLE 1

Viscoelastic properties and apparent viscosities of various formulations; calcium-cross-linked of VLVG and LVG alginate

| Name | Type of Alginate | Alginate MW | Alginate (% (w/v)) | *$Ca^{2+}$ (Calcium Gluconate) (% (w/v)) | Appearance | Viscosity (at 10 1/s), Pa*s | Shear stress (at 10 1/s), Pa*s | G' (Pa) at1 Hz | G" (Pa) at1 Hz | G'&G" |
|---|---|---|---|---|---|---|---|---|---|---|
| A | VLVG | 30 kDa | 1.2 | 0.6 | viscous liquid | 0.6588 | 6.017 | 60.27 | 6.596 | G' > G" |
| B− | VLVG | 30 kDa | 1.43 | 0.64 | viscous liquid | 0.9505 | 5.762 | 56.45 | 5.95 | G' > G" |
| B+ | VLVG | 30 kDa | 1.25 | 0.75 | Gel | 2.806 | 14.11 | 229.7 | 44.87 | G' >> G" |
| C | VLVG | 30 kDa | 1.50 | 0.75 | Gel | 2.121 | 8.342 | 128.6 | 24.27 | G' >> G" |
| D | VLVG | 30 kDa | 2.86 | 1.07 | Firm Gel | 4.686 | 25.5 | 504.9 | 95.23 | G' >> G" |
| E | LVG | 100 kDa | 1 | 0.32 | viscous liquid | 1.253 | 5.519 | 7.903 | 2.96 | G' > G" |
| F | LVG | 100 kDa | 1 | 0.25 | Liquid | 0.0597 | 6.38E−03 | 0.07019 | 0.4087 | G" > G' |

*$Ca^{2+}$ (Calcium Gluconate may also be referred to as Calcium D-gluconate (monohydrate) or D-gluconic acid calcium salt, which terms may be used interchangeably) (% (w/v)).
In Table 1:
A refers to a composition comprising VLVG alginate 1.2% w/v and $Ca^{2+}$ (*Calcium Gluconate) 0.6% w/v.
B− refers to a composition comprising VLVG alginate 1.43% w/v and $Ca^{2+}$ (Calcium Gluconate) 0.64% w/v.
B+ refers to a composition comprising VLVG alginate 1.25% w/v and $Ca^{2+}$ (Calcium Gluconate) 0.75% w/v.
C refers to a composition comprising VLVG alginate 1.5% w/v and $Ca^{2+}$ (Calcium Gluconate) 0.75% w/v.
D refers to a composition comprising VLVG alginate 2.86% w/v and $Ca^{2+}$ (Calcium Gluconate) 1.07% w/v.
E refers to a composition comprising LVG alginate 1.0% w/v and $Ca^{2+}$ (Calcium Gluconate) 0.32% w/v.
F refers to a composition comprising LVG alginate 1.0% w/v and $Ca^{2+}$ (Calcium Gluconate) 0.25% w/v.
LVG alginate in final concentration of 1% and 0.22-0.3% $Ca^{2+}$ (Calcium Gluconate) show liquid-like behavior with lower apparent viscosity, lower values of G' (elastic modulus) and G" (viscous modulus); viscous (flow) behavior is dominant, (G" > G'), whereas higher final Ca concentration of 0.32% w/v or higher lead to more viscous materials with higher values of elastic and viscous moduli (G' and G") viscous (flow) behavior prevails, (G" > G') with solid like appearance, tendency to gel.

According to some embodiments, the Maximal Initial concentrations for maximal viscosity and shear stresses for VLVG alginate is about 5.3% w/v, 3% $Ca^{+2}$ (Calcium Gluconate) w/v. Additional heating may enable higher concentrations. For LVG alginate, the respective concentration is ~3% w/v. All solutions are aqueous, in double distilled water (DDW).

In accordance with some embodiments, compositions that are more viscous and have more tendency to gel may be more appropriate to coat a mesh and its surroundings, after the mesh is implanted in the body, than liquid compositions.

According to some embodiments, the methods, kits and devices disclosed herein, may utilize, for intra-body mesh coating, anti-adhesive compositions that are in a gel form, for example compositions "B+", "C" and "D" (as shown in Table 1, FIG. 11A).

Figure 11:
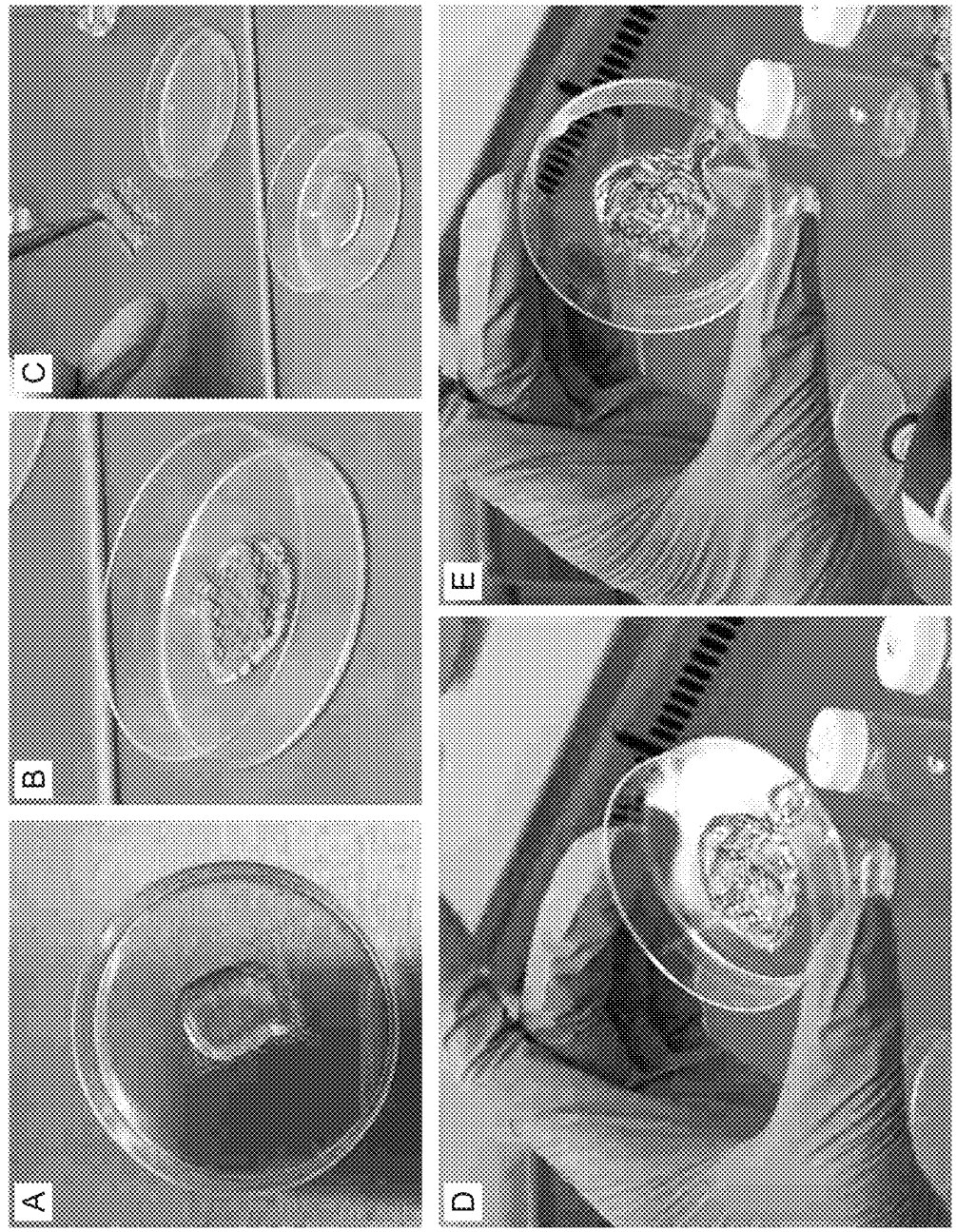
FIGS. 11 A-E show pictures of hydrogel application. VLVG alginate relatively viscous gel administration, high cross-linking; for example, formulations "C" (FIG. 11A), coated mesh with partially cross-linked liquid VLVG alginate, of relatively low viscosity (1.2% VLVG, 0.6% $Ca^{2+}$), before additional cross-linker (FIGS. 11 B, C), and after addition of 1M $CaCl_2$) (FIGS. 11 D, E).

According to some embodiments, the methods, kits and devices disclosed herein, may utilize, for intra-body mesh coating, anti-adhesive compositions that are viscous liquids or even liquids and, after coating the mesh with these compositions, apply another crosslinker-containing composition that will increase the viscosity of the anti-adhesive compositions and convert them to gels. For example, partially-cross linked VLVG 1.43% (w/v) and 0.64% $Ca^{+2}$ Table 1) may be administered on the mesh, and after the administration of liquid-like formulation (FIG. 11 B,C), an additional amount of $Ca^{+2}$ Gluconate/$CaCl_2$) may be administered to formulate a firm gel coating on the mesh (FIG. 11 D,E).

According to other exemplary embodiments, a first layer of partially crossed-linked LVG alginate (prepared for example, by homogenization) at a final concentration of about 1-1.2% (or higher) and about 0.3 (or higher) % $Ca^{+2}$ may be applied to the mesh, and then a second layer of appropriate quantities of 1-3% w/v solution of $Ca^{+2}$ Gluconate or about 1M of $CaCl_2$) solution may be applied (on top of the first layer) to obtain a firm gel coating on the mesh.

According to additional or alternative embodiments (as can be seen from Table 1) another formulation may include VLVG alginate. A benefit of utilizing VLVG alginate (MW<50 kDa) is its clearance from the body through the urinary system.

According to some embodiments, a combination of low and high MW alginates, such as LVG and VLVG alginates may be utilized for intra-body mesh coating.

According to some embodiments, (for example, for the documentation of hydrogel application procedure and layer formation), a color indicator, such as 10 μl methylene blue solution (10 mg/ml in DDW), may be added to the hydrogel.

Figure 8A:
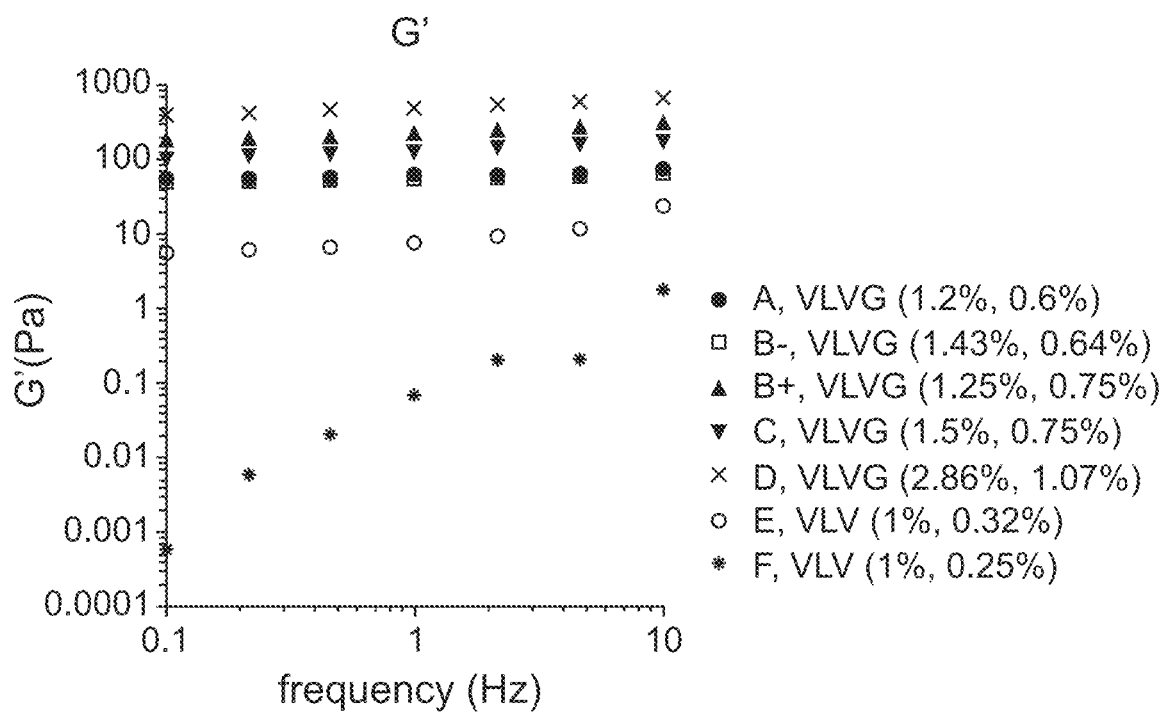
FIGS. 8 A-C show representative graphs for various alginate formulations, G' and G" as functions of frequency (FIGS. 8A and 8B respectively), viscosity as function of shear rates (FIG. 8C)
Figure 8B:
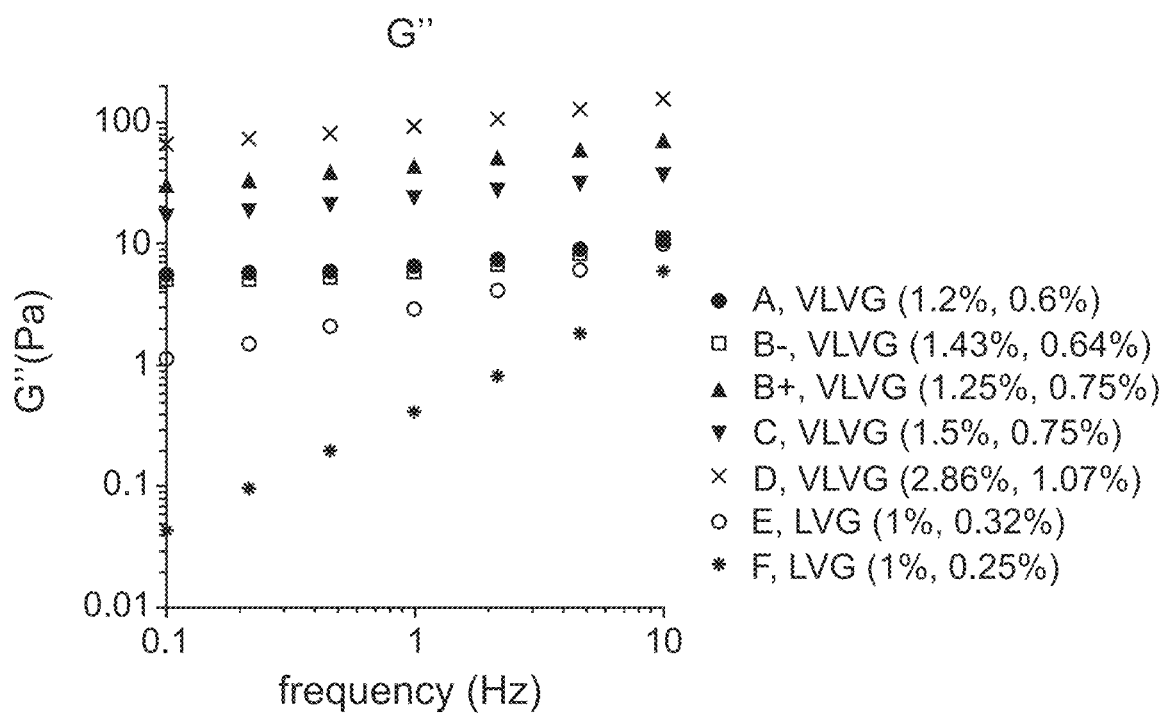
Figure 8C:
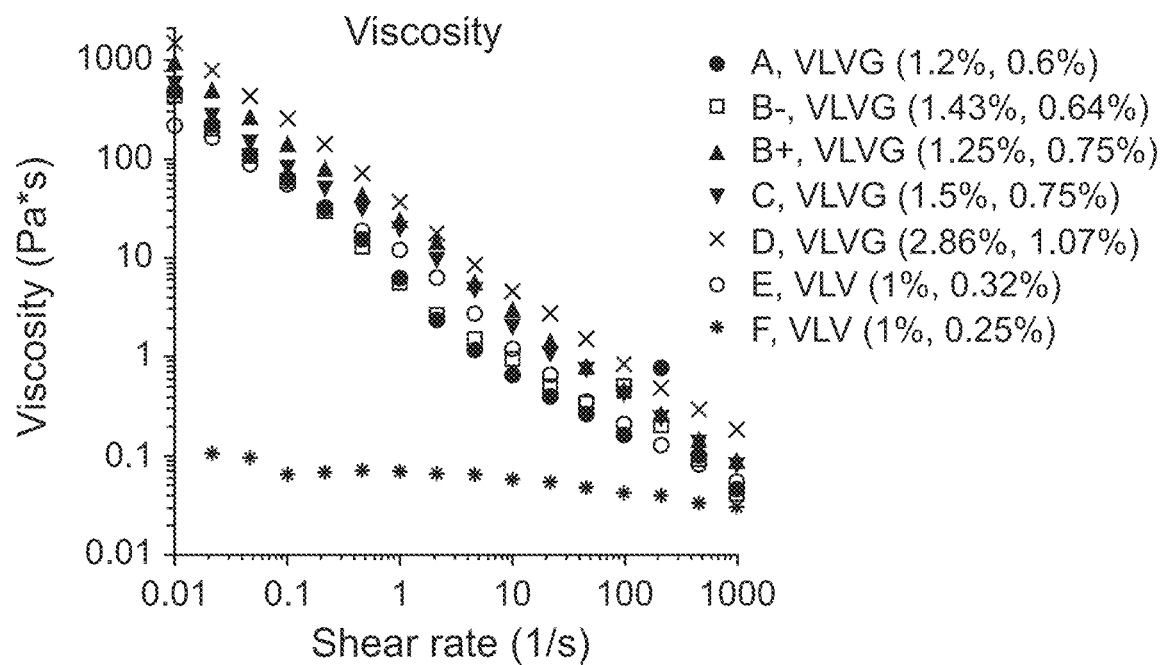

Reference is now made to FIGS. 8 A-C, which show representative graphs for various alginate formulations, storage modulus G' loss modulus and G" as functions of frequency (FIGS. 8A and 8B respectively), viscosity as a function of shear rates (FIG. 8C) of compositions "A", "B−", "B+", "C", "D", "E" and "F" (see Table 1). For VLVG formulations, the higher cross-linked formulations (B+, C, D) show higher storage and loss modulus at all frequencies, compared to other examined VLVG formulations (A, B−). The apparent viscosities of higher cross-linked formulations (B+, C, D) are also shown to be higher, compared to other formulations (A, B−).

For LVG, the formulation of higher Calcium concentration (E) shows lower G' and G" modulus compared to VLVG formulations; however, the apparent viscosity is relatively similar to lower cross-linked formulations (A, B−). Specifically, the LVG alginate formulation of low Calcium concentration (0.25%), liquid-like (F) shows different behavior compared to all other formulations, with lower values of G', G", lower viscosity and negligible response to shear rate.

Figure 9A:
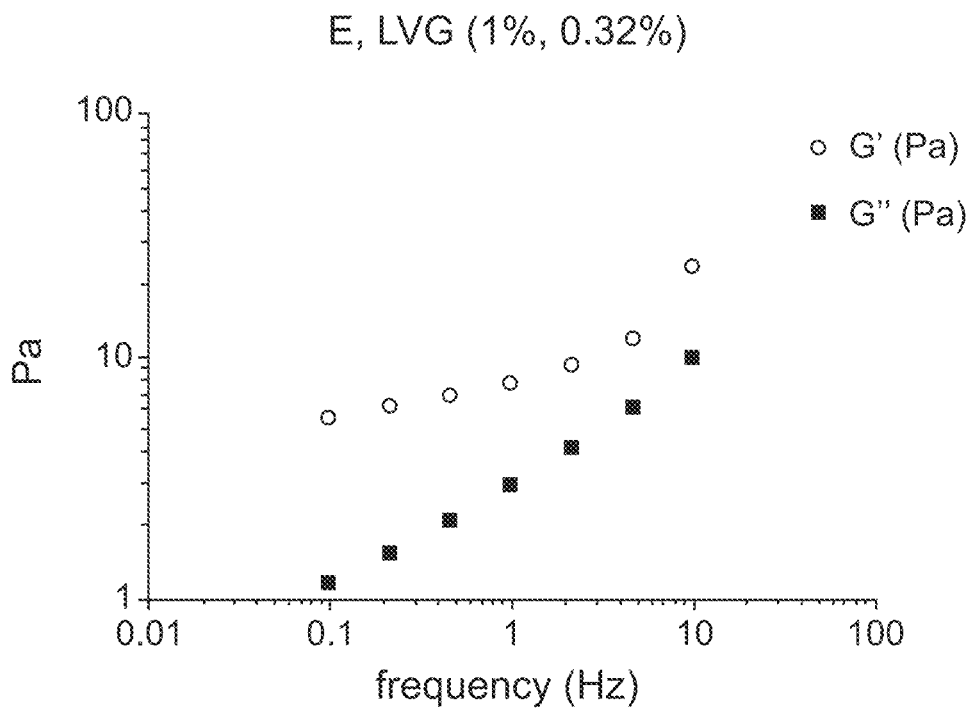
FIG. 9A—composition "E" and FIG. 9B—composition "F" (see Table 1)
Figure 9B:
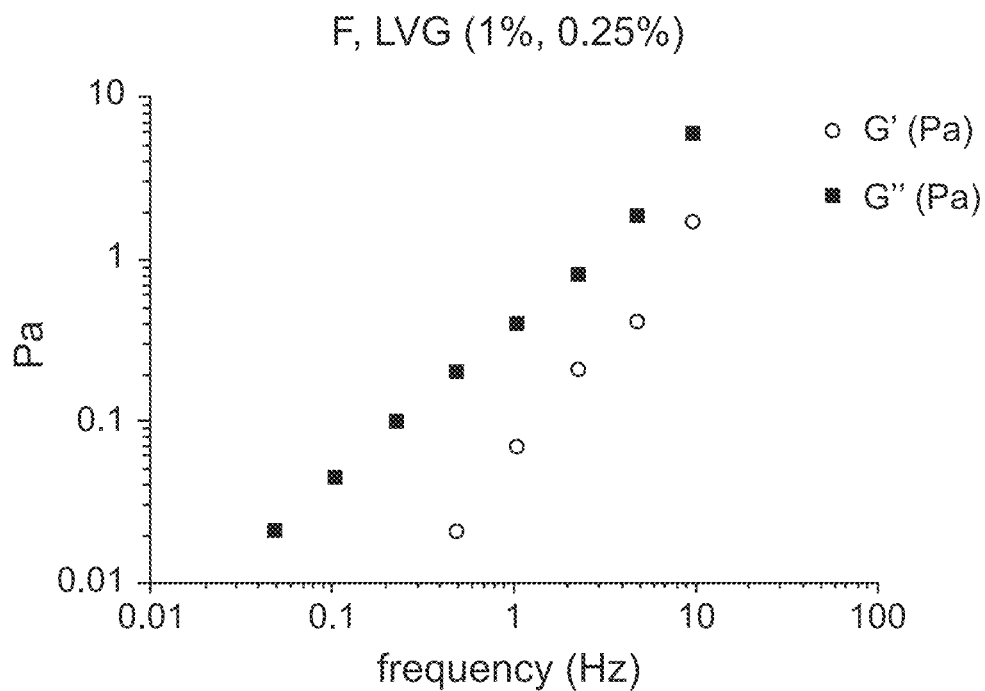
FIGS. 9 A-B show representative mechanical spectra, oscillatory behavior of calcium-cross-linked solutions of LVG (100 kDa) alginate.

Reference is now made to FIGS. 9 A-B, which show representative mechanical spectra, oscillatory behavior of calcium-cross-linked solutions of LVG (100 kDa) alginate: FIG. 9A—composition "E" and FIG. 9B—composition "F" (see Table 1). Small deformation oscillatory measurements are presented in terms of the storage modulus, G' (elastic response), and the loss modulus, G" (viscous response), as functions of angular frequency. G' is used as the primary indicator of a gel-like (structured) system. In 0.32% $Ca^{2+}$ cross-linked LVG alginate (composition "E"), G' exceed G", elastic behavior dominates (storage modulus is dominant, G'>G", FIG. 9A). In 0.25% $Ca^{2+}$ cross-linked LVG alginate (composition "F"), G" and G' values were lower, and viscous (flow) behavior prevails, (G">G', FIG. 9B).

Figure 10A:
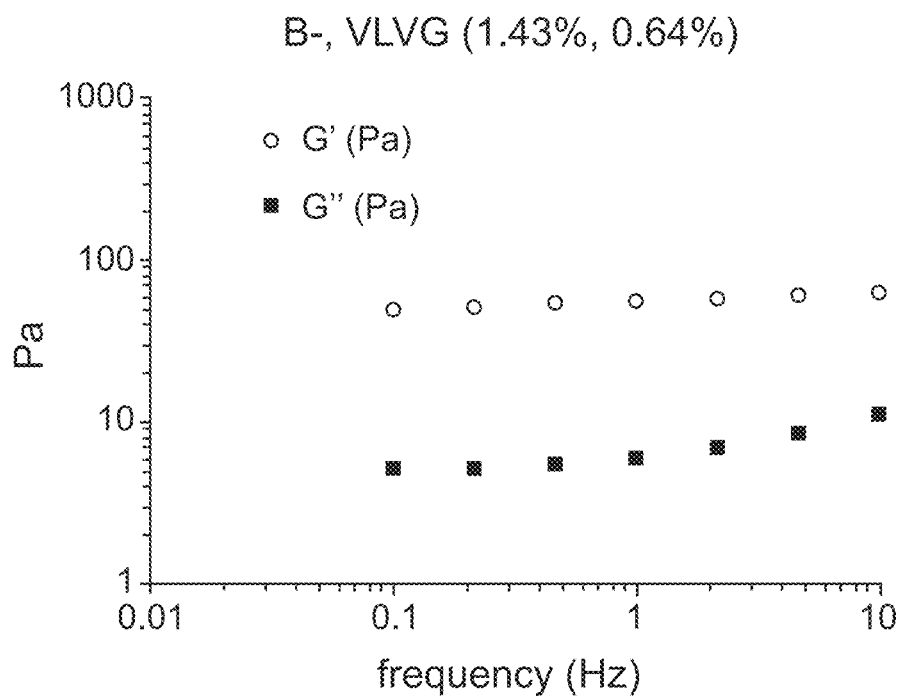
FIG. 10A—composition "B−" and FIG. 10B—composition "B+" (see Table 1)
Figure 10B:
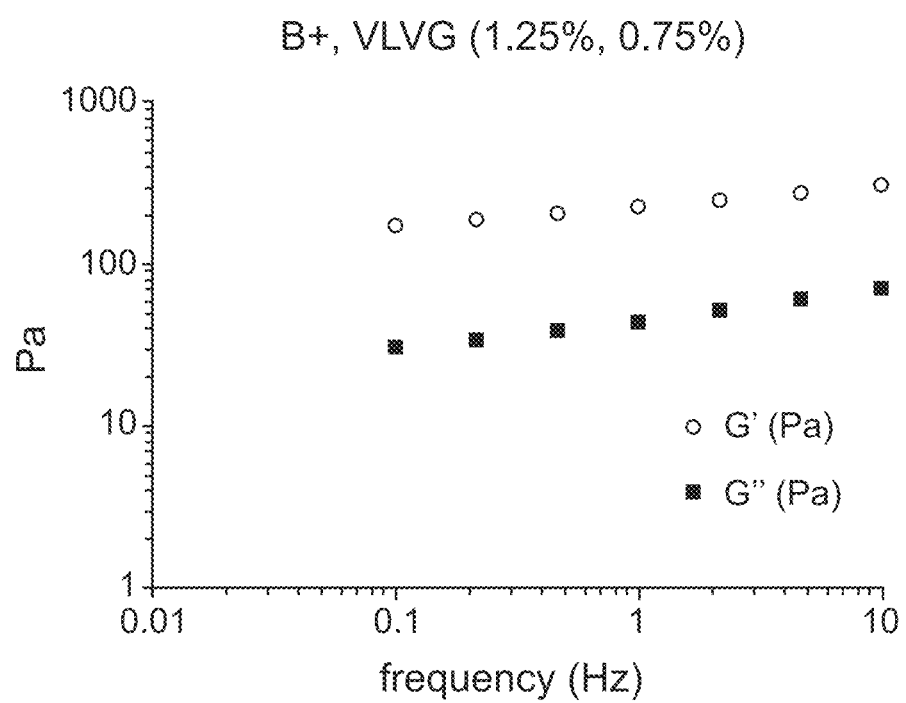
FIGS. 10 A-B show representative mechanical spectra, oscillatory behavior of calcium-cross-linked solutions of VLVG (30 kDa) alginate.

Reference is now made to FIGS. 10 A-B, which show representative mechanical spectra, oscillatory behavior of calcium-cross-linked solutions of VLVG (30 kDa) alginate: FIG. 10A—composition "B−" and FIG. 10B—composition "B+" (see Table 1). Small—deformation oscillatory measurements are presented in terms of the storage modulus, G' (elastic response), and the loss modulus, G" (viscous response), as functions of angular frequency. G' is used as the primary indicator of a gel-like (structured) system.

The two formulations present partially cross-linked alginate solution ("B−"), compared to cross-linked alginate solution to a higher extent ("B+"). In both, G' exceed G", elastic behavior dominates (storage modulus is dominant, G'>G"). The higher degree of cross-linking results in higher values of storage and loss moduli, and higher viscosity values (see Table 1).

FIGS. 11 A-E show pictures of hydrogel applications. VLVG alginate relatively viscous gel administration, high cross-linking (FIG. 11A), coated mesh with partially cross-linked liquid VLVG alginate, of relatively low viscosity (1.2% VLVG, 0.6% $Ca^{2+}$, such as composition "A" in Table 1), before additional cross-linker (FIGS. 11 B, C)—acts as liquid, thus lifting the mesh would leave most of it on the plate (FIG. 11C); and after addition of 1M $CaCl_2$) (FIGS. 11 D, E).

The methods, kits and devices disclosed herein, may utilize, for intra-body mesh coating, anti-adhesive compositions that are in a gel form, for example compositions "B+", "C" and "D" (as shown in Table 1, FIG. 11A).

Another example: partially-cross linked VLVG 1.2% (w/v) and 0.6% $Ca^{+2}$ (such as composition "A" presented in Table 1) may be administered on the mesh, and after the administration of liquid-like formulation (FIG. 11 B, C), an additional amount of $Ca^{+2}$ Gluconate/$CaCl_2$) may be administered to formulate to obtain a firm gel coating on the mesh (FIG. 11 D, E).

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof. Unless otherwise defined, all technical and scientific terms used herein have the same meaning as commonly understood by one of ordinary skill in the art to which this invention belongs.

Unless specifically stated otherwise, as apparent from the following discussions, it is appreciated that throughout the specification discussions utilizing terms such as "processing", "computing", "calculating", "determining", "estimating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

What is claimed is:

1. A method for reducing or treating post-operative adhesions in a target site within a body of a subject, the method comprising:
    introducing an applicator into a target site within a body of a subject, wherein the applicator is configured for applying an anti-adhesive composition to an implanted medical device fixed and deployed in the target site; and
    applying in situ the anti-adhesive composition onto the implanted medical device, wherein said method is performed during or following an interventional medical procedure, and
    wherein said applying in situ the anti-adhesive composition onto the implanted medical device comprises the following steps:
        a. spreading, onto the implanted medical device, a first composition comprising an anti-adhesive substance, wherein the anti-adhesive substance is a viscous liquid comprising alginate that has been partially crosslinked using calcium gluconate, such that the alginate has a $Ca^{2+}$ concentration of about 0.25-3% w/v; and
        b. applying, onto the first composition, a second composition comprising a bivalent cation crosslinker, thereby transforming the viscous liquid into a gel.

2. The method of claim 1, further comprising applying the anti-adhesive composition to a tissue and/or an organ in the vicinity of the implanted medical device.

3. The method of claim 1, wherein the medical implant comprises a surgical mesh and/or wherein the medical implant further comprises a mesh fixation element.

4. The method of claim 3, further comprising deploying and fixing the mesh in the target site prior to applying the anti-adhesive composition thereon.

5. The method of claim 1, wherein the alginate has a MW in the range of 5-50 kDa, a MW in the range of 50-400 kDa or a combination thereof.

6. The method of claim 1, wherein the bivalent cation crosslinker comprises $Ca^{2+}$, $Ba^{2+}$, $Mg^{+2}$ combination thereof.

7. The method of claim 1, wherein the alginate has a MW in the range of 50-400 kDa at a concentration of about 0.7-2.0% (w/v).

8. The method of claim 7, wherein the alginate has a MW in the range of 50-400 kDa at a concentration of about 0.7-2.0% (w/v) and Ca' cations at a concentration of about 0.25-1% (w/v).

9. The method of claim 1, wherein the alginate has a MW in the range of 5-50 kDa at a concentration of about 1.0-5.0% (w/v).

10. The method of claim 9, wherein the alginate has a MW in the range of 5-50 kDa at a concentration of about 1.0-5.0% (w/v) and Ca' cations at a concentration of about 0.5-3% (w/v).

11. The method of claim 6, wherein the $Ca^{2+}$ cations originate from calcium chloride ($CaCl_2$)).

12. The method of claim 1, wherein the applicator is selected from the group consisting of a sprayer, a racket, a sprinkler, a nebulizer, and any combination thereof.

* * * * *